US005629423A

United States Patent [19]
Klein et al.

[11] Patent Number: 5,629,423
[45] Date of Patent: May 13, 1997

[54] ASYMMETRIC SYNTHESIS OF CHIRAL SECONDARY ALCOHOLS

[75] Inventors: J. Peter Klein, Vashon; Alistair J. Leigh, Brier; John Michnick; Anil M. Kumar, both of Seattle; Gail E. Underiner, Brier, all of Wash.

[73] Assignee: Cell Therapeutics, Inc., Seattle, Wash.

[21] Appl. No.: 449,400

[22] Filed: May 23, 1995

Related U.S. Application Data

[63] Continuation-in-part of Ser. No. 242,944, May 16, 1994, abandoned.
[51] Int. Cl.$^6$ ........................ C07D 513/04; C07D 301/00
[52] U.S. Cl. ........................ 544/48; 549/518; 558/52; 560/266
[58] Field of Search ........................ 549/518; 558/52; 560/266; 544/48

[56] References Cited

U.S. PATENT DOCUMENTS 5,243,096  9/1993  Takono et al. ........................ 549/519

FOREIGN PATENT DOCUMENTS

| 455473 | 11/1991 | European Pat. Off. | 549/518 |
| 62-108854 | 5/1987 | Japan | 558/52 |
| 01096176 | 4/1989 | Japan | 549/518 |
| 01230567 | 9/1989 | Japan | 549/518 |
| WO89/10350 | 11/1989 | WIPO | 549/518 |

OTHER PUBLICATIONS

Chini et al., *Tetrahedron Letters*, vol. 32, No. 45, pp. 6617–6620, "Stereo–and Regioselective Metal Salt–Catalyzed Alkynylation of 1,2–Epoxides", 1991.

Ellis et al., *Org. Syn.*, vol. 63, pp. 140–145, "Optically Active Epoxides From Vicinal Diols Via Vicinal Acetoxy Bromides: The Enantiomeric Methyloxiranes", 1984.

Hillis et al., *J. Org. Chem.*, vol. 46, pp. 3348–3349, "Improved Preparation of (+)–(R)–Methyloxirane", 1981.

Johnston et al., *Can. J. Chem.*, vol. 57, pp. 233–235, "Facile Syntheses of the Enantiomers of Sulcatol", 1979.

Lampilas et al., *Tetrahedron Letters*, vol. 33, No. 6, pp. 773–780, "Convergent Stereospecific Total Synthesis of Monochiral Monocillin I Related Macrolides", 1992.

Mori et al, *Tetrahedron Letters*, vol. 41, No. 3, pp. 541–546, "Synthesis of the Enantiomers of CIS-2-Methyl-5-Hexanolide, The Major Component of the Sex Pheromone of the Carpenter Bee", 1985.

Nokami et al., *Chemistry Letters*, pp. 1103–1106, "A New Approach to the Synthesis of γ–Hydroxy–α, β–unsaturated Macrolides and (–)–Pyrenophorin", 1994.

*Primary Examiner*—Joseph E. Evans
*Attorney, Agent, or Firm*—Stephen Faciszewski

[57] ABSTRACT

A process for synthesizing enantiomerically pure chiral secondary alcohol compounds linked to a heterocyclic core moiety, using a natural chiral molecule starting material. The inventive process is particularly useful for bulk manufacturing of chiral secondary alcohol compounds.

30 Claims, 3 Drawing Sheets

ASYMMETRIC SYNTHESIS OF CHIRAL SECONDARY ALCOHOLS

This application is a continuation-in-part of application Ser. No. 08/242,994 filed May 16, 1994, now abandoned.

TECHNICAL FIELD OF THE INVENTION

The invention provides a process for synthesizing enantiomerically pure chiral secondary alcohol compounds linked to a heterocyclic core moiety, using a natural chiral molecule starting material. The inventive process is particularly useful for bulk manufacturing of chiral secondary alcohol compounds.

BACKGROUND OF THE INVENTION

It is common practice to synthesize and market a drug possessing a chiral center as its racemate. If an enantiomerically pure molecule is needed, one often synthesizes the racemate and then chirally separates the enantiomers. Manufacturing racemates means that a quantity of compound contains an equivalent weight (approximately) of isomers, one of which often has no therapeutic value and potentially may cause unsuspected side effects. For example, the sedative thalidomide was marketed as a racemate. Sedative activity resided in the R-isomer, but the contaminating S-isomer is a teratogen and is thought to cause birth defects in babies born to mothers using this drug. The R,R-enantiomer of the tuberculostatic Ethambutol can cause blindness. The lethal side effects associated with the non-steroidal anti-inflammatory drag benoxaprofen (Oraflex) might have been avoided had the drug been sold as a pure enantiomer.

However, the issue of enantiomeric purity is not limited to the field of pharmaceuticals. For example, ASANA ($^i$Pr= isopropyl) is a synthetic pyrethroid insecticide which contains two asymmetric centers. The potent insecticidal activity resides overwhelmingly in just one of four possible stereoisomers. Moreover, the three non-insecticidal stereoisomers exhibit cytotoxicity in certain plant species. Therefore, ASANA can only be sold as a single stereoisomer because the mixed stereoisomers would not be suitable. Therefore, there is a need to manufacture certain compounds with at least one chiral center as pure specific enantiomeric compounds and not as a racemate.

The pharmaceutical compound (R)-1-(5-hydroxyhexyl)-3,7-dimethylxanthine (described in WO93/17684, and in U.S. patent application 08/307,554, filed Sep. 16, 1994, the disclosure of which is incorporated in its entirety by reference herein) is useful for a wide variety of therapeutic indications, including, for example, sepsis and sepsis syndrome, trauma, increasing the production of multilineage cells after cytoreductive therapies, promoting engraftment after bone marrow transplantation, and alleviating the toxic side effect of interleukin-2 (IL-2), amphotericin B, cyclosporin A or FK506 therapy and granulocyte macrophage colony stimulating factor (GM-CSF) therapy. The synthesis procedure described in the foregoing International and U.S. Patent Applications is capable of achieving a chiral purity of about 95% for the R enantiomer. Also, the process disclosed has limited application for producing larger quantities of product. Therefore, there is a need in the art to improve upon this commercially viable synthetic process for producing a compound of higher enantiomeric purity.

Large-scale manufacturing of synthetic compounds, particularly compounds having a high enantiomeric purity, is usually not a simple process of increasing reagent quantitites or reaction vessel volumes. In fact, often the scale-up of synthetic protocols results in unexpected and undesirable results and/or contaminants, failing to provide commercially viable manufacturing methods. The invention addresses this need, providing a less expensive synthetic process utilizing readily available (or readily prepared) starting materials. The inventive process is directed to synthetic procedures for preparing products and isolating certain intermediates in significantly larger quantities with far higher yields and greater purity, being heretofore unknown.

Others have described synthetic processes for making chiral enantiomers using stereo specific routes involving catalytic activation, one such process is discussed in Lampilas et al., "Convergent Stereospecific Total Synthesis of Monochiral Monocillin I Related Macrolides," *Tetrahedran Letters*, Vol. 33, No. 6, pp. 777–780 (1992). However, Lampilas et al. is limited to reacting R (or S) propylene oxide with a lithium salt of a branched alkoxyalkynyl and subsequent preparation of a primary alcohol used in successive synthetic steps to obtain the disclosed monochiral Monocillin I and corresponding derivatives.

Mori et al., "Synthesis of the Enantiomers of cis-2-Methyl-5-Hexanolide, the Major Component of the Sex Pheromone of the Carpenter Bee," *Tetrahedron*, vol. 41, No.3, pp. 541–546 (1985), discloses synthesis of bichiral (2R,5S)-2-Methyl-5-hexanolide from an ethyl (2)-lactate starting material. Using a published process for preparing (S-)-propylene oxide, Mori et al. discloses converting an intermediate ester product to the corresponding (R-)-propylene oxide, having an optically determined enantiomeric purity of 97.3%. Mori et al. is limited to preparing the disclosed pheromone via the propylene oxide intermediate.

Johnston et al., "Facile Syntheses of the Enantiomers of Sulcatol," *Can. J. Chem.*, vol. 75, pp. 233–235 (1979), discloses a synthesis for an aggregation pheromone, Sulcatol, prepared from methyl oxirane enantiomers. The R-(+)-methyl oxirane was prepared from S-(−)-ethyllactate, first converting it to tosylate and subsequently reacting the tosylate to obtain a the corresponding oxirane. The disclosed tosylate yield is 71% (based on a lactate starting material) and the resulting methyloxirane was obtained in a disclosed 50% yield (based on tosylate starting material). Johnston et al. specifically requires depressed reaction temperatures and very long reaction times (8 days). Johnston et al. is limited to specific process conditions that are non-scalable for commercial purposes and that require reaction conditions not embraced in the inventive synthetic procedure for preparing chiral propylene oxide.

Hillis et al,. "Improved Preparation of (+)-(R)-Methyloxirane," *J. Org. Chem.*, vol. 46, pp. 3349–3352 (1981), disclose processes for preparing (+)-R-methyloxirane from (+)-(S)-lactate in several process steps. In the disclosed process steps, methanesulfonyl chloride was allowed to react with the lactate starting material in toluene, producing an intermediate, ethyl (−)-(S)-2-(mesyloxy) propanoate. The intermediate was then reacted with LiAlH$_4$ in THF, resulting in an alcohol precursor. The alcohol precusor was reacted in a distillation process with KOH to obtain the desired oxirane product. Hillis et al. is limited to a process for obtaining the disclosed oxirane product via the specific steps provided. Hillis et al. do not disclose a method for preparing chiral secondary alcohols or derivatives thereof. Furthermore, the disclosed process for preparing the oxirane products is not the inventive process. The disclosed process requires formation of a sulfonyl intermediate and distillation of a final product, the latter of which is particularly unadaptable for commercial preparation.

Ellis et al., "Optically Active Epoxides from Vicinal Diols via Vicinal Acetoxy Bromides: The Enantiomeric Methyl oxiranes," *Org. Syn.*, vol. 63, pp. 140–145 (1984), discloses synthetic protocols for preparing S-(−)-methyloxirane from ethyl-L-(−)-lactate through esterification, halogenation and corresponding reduction reactions. Disclosed yields for the propylene oxide intermediate are substantially less than the yields permitted by the inventive method. The disclosed synthesis requires reducing the lactate ester using lithium aluminum hydride, followed by simultaneously esterifying and halogenating an intermediate diol.

The process disclosed in Ellis et al. is limited to the specifc synthetic steps disclosed. These disclosed steps differ from the inventive process in that they do not disclose preparing R-(+)-propylene oxide via the inventive process or subsequently reacting in the R-(+)-propylene oxide in a series of reactions to obtain a secondary chiral alcohol.

Nokami et al., "A New Approach to the Synthesis of α-Hydroxy-α,β-unsaturated Macrolides and (−)-Pyrenophorin...", *Chem. Letters*, pp. 1103–1106 (1994), discloses a process for preparing (+)- and (−)-Pyrenophorin, in which a first process step includes treating S-(−)-propylene oxide with lithium 3-tetrahydropyranyloxypropynylide to obtain an optically active alcohol. The resulting alcohol is converted to a corresponding benzl ether, and the THP-ether hydrolyzed to the corresponding alcohol. Other resulting intermediates are prepared in sequential synthetic steps to obtain a final product, (+)-/(−)-pyrenophorin. Nokami et al. is limited to preparing S-(−)-propylene oxide and other intermediates in process steps different than permitted by the inventive process to obtain a chemically different product from compounds produced by the inventive process.

The inventive process therefore provides a heretofore unknown method for preparing chiral secondary alcohols and selectively preparing and isolating intermediates thereof. The process addresses known, commercially-limiting process steps, including restrictive and unscalable reaction conditions, undesireable yields and by product contamination of desired products.

SUMMARY OF THE INVENTION

The present invention provides a process for asymmetric synthesis of chiral secondary alcohols (and chiral acetoxy derivatives thereof), having protected or unprotected chemical structures. The inventive process involves a series of steps, which collectively permit high yields and purity of at least one enantiomer. A first step includes providing a chiral α-hydroxy ester starting material of variable chain length. A starting material stereochemistry is opposite to secondary alcohol product stereochemistry. Next, the starting material hydroxyl group is activated with a leaving group and the starting material ester group is converted to a first intermediate alcohol product. The first intermediate alcohol product is then deprotonated with a base and in an intramolecular reaction between the first intermediate alcohol and the leaving group to form a chiral oxirane. This reduction step also serves to invert the stereochemistry of the starting material.

Preparation of a second reaction product in the inventive process involves providing a terminal, $C_{3-10}$ alkynyl primary alcohol. A first primary hydroxyl group of the alkynyl alcohol is converted to an alkali-stable group, forming an alkynyl intermediate. Next, the alkynyl intermediate is treated with a strong base, resulting in formation of an acetylide anion salt, having a mono- or di-valent cation. The acetylide anion salt (the second reaction product) is then coupled to the chiral oxirane, prepared above. This step forms a second intermediate alcohol, having the alkynyl and alkali-stable groups.

In the next step, the alcohol group of the second intermediate alcohol is converted to an intermediate ester. The intermediate ester retains both the alkynyl and alkali-stable groups. The unsaturated alkynyl group (triple bond) is hydrogenated, first to an alkenyl and then to an alkyl, saturated carbon-carbon bond. Subsequently, the alkali-stable group is converted to a second primary hydroxyl group, leaving an alkyl intermediate ester having a second primary hydroxyl group. Preferably, this step is hydrogenolysis or mild acid hydrolysis of a corresponding alkali-stable ether, protecting the first primary hydroxyl group.

The second primary hydroxyl group is then replaced with a terminal leaving group, forming an ester precursor. Preferred leaving groups include, but are not limited to: a halide (resulting in chiral, ester-halide precursor), arylsulfonate or alkylsulfonate (most preferably, halide). The terminal leaving group of the ester precursor is replaced with a core moiety substituent (either commercially available or prepared by another synthetic process). Finally, the ester precursor is reduced to obtain the secondary alcohol product in high yield and purity.

The present synthetic process provides a commercially viable and cost-effective method for producing chiral secondary alcohols, yielding a high enantiomeric excess (ee) of a given enantiomer. Preferably, the ee of the desired enantiomer is greater than 99%, providing that the chiral α-hydroxy ester starting material has an equivalent ee).

The ester precursor, having a terminal leaving group, can be coupled to, for example, a hetero atom of a heterocyclic moiety, such as the N1 nitrogen atom of a xanthine moiety, by reacting the terminal leaving group (preferably an ester-halide precursor), in an appropriate solvent, such as DMSO, DMF, ethanol, isopropanol or other alcohol (most preferably, DMSO) with the heterocyclic moiety, thereby forming a chiral ester precusor. As discussed above, the ester precursor can then be hydrolyzed to form the chiral secondary alcohol, substituted by a heterocyclic moiety.

In addition, the inventive process is useful for preparing chiral oxiranes in substantial yield and purity on a commercial scale. In the above steps, the chiral oxirane is prepared and isolated as a high-purity intermediate product. The resulting process has advantages not previously observed in conventional preparation methods.

BRIEF DESCRIPTION OF THE DRAWING

FIGS. 1a–1c show a schematic diagram for a representative process of the invention as discussed in detail in Example I: synthesis of (R)-1-(5-acetoxyhexyl)-3,7-dimethylxanthine and the pharmaceutical compound (R)-1-(5-hydroxyhexyl)-3,7-dimethylxanthine according to the inventive method described herein.

DETAILED DESCRIPTION OF THE INVENTION

The present invention provides a synthetic process for synthesizing chiral secondary alcohols, chiral oxirane intermediates and chiral esters of these chiral secondary alcohols. In addition, a resulting chiral hydroxyalkyl may be halogenated and coupled to a heterocyclic moiety, such as a xanthinyl moiety or any other nucleophilic moiety that can displace the terminal leaving group in a substitution reaction.

Generally, as discussed above, the inventive process involves a series of steps, which collectively permit high yields and purity of at least one enantiomer of both chiral, secondary alcohol (and derivatives thereof) and chiral oxirane (epoxide) products. Synthetic process steps include: first, providing a chiral α-hydroxy ester starting material of viable chain length wherein a starting material stereochemistry is opposite a secondary alcohol product stereochemistry.

In the first step, a hydroxyl group of an α-hydroxy ester starting material is activated with a leaving group to form an intermediate activated ester. Procedurally, the α-hydroxy ester is combined with a sulfonyl acid chloride in the presence of a base, with or without a solvent (if present, preferably an ester, ether, or hydrocarbon, more preferably toluene solvent) at temperatures ranging between 20°–50° C. for 4–8 hours. Subsequent addition of mineral acid and washing the organic phase with a salt solution removes excess base. The product may be isolated by solvent removal as required. Preferred α-hydroxy ester starting materials include R- or S-ethyl lactate and leaving groups include but are not limited to sulfonyl acid chlorides, notably, p-toluenesulfonyl chloride and methanesulfonyl chloride. Representative, preferred bases are pyridine and trialkylamines. Although a solvent is not required, solvents may be at least one of an ester, ether or hydrocarbon solvent. Preferred mineral acids and salt solutions include, for example, hydrochloric acid and sodium chloride or calcium chloride, respectively. In a preferred embodiment, the α-hydroxy ester is for example ethyl (S)-(−)-lactate, the leaving group is p-toluenesulfonyl chloride and a resulting ester product is ethyl (S)-2-p-toluenesulfonyloxy propionate. A schematic representation of this preferred reaction is shown below.

ethyl (S)-2- p-toluenesulfonyloxypropionate

The intermediate activated ester is then converted to a first intermediate alcohol product by reacting the intermediate activated ester with a reducing agent in a solvent. Preferably, the activated ester and reducing agent are reacted at a temperature ranging from −40° C. to +80° C. Excess reducing agent is removed by addition of a suitable ketone reagent and addition of a solubilizing agent to hydrolyze any reducing agent-derived residue at a hydrolysis temperature ranging from 0° C. to +40° C. The resulting reaction mixture is filtered to remove precipitates and washed with aqueous solution. The solvent is finally removed to isolate the first intermediate primary alcohol. Preferred reducing agents are, for example, borane-tetrahydrofuran, borane-methylsulfide, diisobutyl aluminium hydride, sodium bis (2-methoxyethoxy) aluminium hydride, and sodium borohydride activated with methanol or acetic acid. Representative solubilizing agents include, but are not limited to, sodium carbonate, sodium hydroxide, hydrochloric acid, sulfuric acid and potassium sodium tartrate. Solvents may be at least one ether or hydrocarbon solvent, although other solvents are within the scope of the invention.

In a deprotonation reaction, the first intermediate alcohol product is reacted with a base to form an alkoxide, which reacts in an intramolecular substitution reaction with the leaving group to form a chiral oxirane. This substitution step also inverts the stereochemistry of the starting material.

Reacting the first intermediate alcohol product and a base in a solvent, while maintaining a solution temperature ranging from 0° C. to 90° C. yields the desired oxirane product, thereby inverting the stereochemistry of the starting material. The resulting oxirane is isolated by distillation from the heated reaction or by extraction into a solvent, with the solvent/oxirane mixture being subsequently distilled. Representative bases include: sodium, potassium or calcium hydroxide, potassium tert-butoxide, potassium hydride and sodium or potassium carbonate. Solvents may be selected from aqueous, hydrocarbon, ether, polar aprotic and alcohol solvents. Preferred solvents include, but are not limited to: water and toluene. Schematically, a preferred process for preparing (R)-(+)-propylene oxide from a crude tosyl alcohol, inverting the chirality of the molecule, is shown below as (part a):

"lithiate intermediate"

↓ H₂O (R)-1-benzyloxy-5-hydroxy-2-hexyne + LiOH (in water)

Or alternatively, a preferred part a of this step is schematically represented below:

Preparation of a second reaction product in the inventive process involves providing a terminal, $C_{3-10}$ alkynyl primary alcohol. A first primary hydroxyl group of the alkynyl alcohol is converted to an alkali-stable group (preferably ether or acetal), forming an alkynyl intermediate. Most preferred alkynyl intermediates are ethers.

The alkynyl intermediate is prepared using a $C_3$ alkynyl primary alcohol and reacting this alcohol with an electrophile. Generally, in the inventive process, electrophiles include, but not are not limited to, benzyl halides (preferably chloride, bromide or iodide) and are reacted with the alkoxide generated from the alkynyl alcohol with strong bases. Representative bases are potassium or sodium hydroxide, potassium carbonate and sodium hydride. Reaction times are decreased by the presence of tetraalkyl and arylalkyl ammonium salt phase transfer catalysts. Preferable catalysts may be tetrabutyl ammonium bromide, tetrabutyl ammonium hydrogen sulfate, tetrabutyl ammonium chloride, tributylmethyl ammonium chloride and tricaprylmethylammonium chloride. Catalysts such as alkali metal iodides, which generate benzyl iodide in situ, also facilitate ether formation. Suitable solvents are ethers or hydrocarbons (toluene, hexane, heptane) and aqueous bases where applicable. Suitable reaction temperatures vary between 10° and 90° C., and preferably, the alkynyl intermediate is isolated by extraction into an organic solvent with subsequent removal of the solvent by distillation. The most preferred reagents may be sodium hydroxide (base), tetrabutyl ammonium bromide, benzyl chloride (catalysts) and propargyl alcohol (primary alcohol).

In a preferred process, propargyl alcohol is reacted with benzyl chloride according to the following mechanism:

Next, the alkynyl intermediate is treated with a strong base, resulting in formation of an acetylide anion salt, having a mono- or di-valent cation. The alkynyl intermediate may be deprotonated with strong bases such as alkyl lithiums in hydrocarbon and ether solvents, metal amides in polar aprotic solvents and alkali metals in ammonia, naphthalene and styrene. Examples of solvents are heptane, tetrahydrofuran, dimethyl sulfoxide and N-methyl pyrrolidinone. Suitable reaction temperatures range from –20° to 70° C. The acetylide anion is used in solution for the next step. Preferred reagents are butyllithium (strong base) and heptane (solvent).

A preferred process for preparing a lithium anion salt of benzylpropargylether is schematically represented as part b, above.

The acetylide anion salt (the second reaction product) is then coupled to the chiral oxirane, prepared above. This step forms a second intermediate alcohol, having the alkynyl and alkali-stable groups. The acetylide anion is coupled to the chiral oxirane in a solvent. Preferred solvents include polar aprotic solvents or a Lewis acid in an ether solvents. Representative examples of preferred solvents are dimethyl sulfoxide, N-methyl pyrrolidinone, tetrahydrofuran and dioxane and Lewis acids may be, inter alia, boron trifluoride etherate and lithium perchlorate. Preferred reaction temperatures range from −20° to 65° C. The reaction product is isolated by extraction with ether or ester solvents and subsequently distilled.

Preferred reagents used in representative processes of the invention are chosen to give the optimum regioselectivity in the opening of the chiral epoxide, such as, for example, dimethylsulfoxide, N-methyl pyrrolidinone and lithium perchlorate in tetrahydrofuran/hexane give 0.15–0.35% of 5-hydroxy-1-benzyloxy-4-methyl-2-pentyne relative to 5-hydroxy-1-benzyloxy-2-hexyne. This equates to a regioselectivity of 99.65–99.85%. Schematically a preferred process for coupling the chiral oxirane to the acetylide anion is shown in part c, above.

In the next step, the alcohol group of the second intermediate alcohol is converted to an intermediate ester. The intermediate ester retains both the alkynyl and alkali-stable groups. Generally, the alcohol group is converted to an ester by reaction with acid anhydrides or acid halides in the presence or absence of acids or bases. Representative acids or bases include, but are not limited to, acetic anhydride with phosphoric acid, perchloric acid, sulfuric acid or dimethyl aminopyridine. Preferably, acetyl chloride is used with triethylamine and dimethylaminopyridine. Reaction temperatures may range from 0° to 80° C. In this process step, excess reagent is removed by the addition of sodium carbonate or sodium bicarbonate. This reaction may be performed in the absence of solvents or in a solvent system, preferably, hydrocarbon solvents. The solvents may be heptane, toluene or ester solvents such as ethyl acetate. The product is isolated by distillation. Most preferred reagents may be sulfuric acid, acetic anhydride and sodium carbonate.

Subsequently, the unsaturated alkynyl group is hydrogenated, first to an alkenyl and then to an alkyl, saturated carbon-carbon bond. Prior to reducing the unsaturated bond, the substrate is treated with an aqueous solution of potassium peroxymonosulfate and decolorising charcoal to remove impurities. Alternatively, powdered nickel on a solid support (and similar systems) may also be used. Reduction is achieved using a transition metal catalyst. The transition metal catalysts may be, for example, nickel, palladium metal or hydroxide, platinum metal or oxide, rhodium, or ruthenium and hydrogen at elevated pressures. Corresponding hydrogen pressures generally range from 0 to 150 psi at temperatures at temperatures ranging from 0° to 100 ° C. Alcohols, esters or hydrocarbons and the like are suitable solvents. The reaction can also be performed by transfer hydrogenation using cyclohexene and palladium. Most preferred reagents may be palladium on charcoal, heptane, and hydrogen.

Subsequently, the alkali-stable group is converted to a second primary hydroxyl group, leaving an alkyl intermediate ester having a second primary hydroxyl group. Preferably, this step is one of hydrogenolysis or mild acid hydrolysis of a corresponding alkali-stable ester, protecting the first primary hydroxyl group. This deprotection is achieved using transition metal catalysts such as nickel, palladium metal or hydroxide, platinum metal or oxide, rhodium, or ruthenium and hydrogen. Hydrogen pressures range from 0 to 150 psi at temperatures from 0° to 100 ° C. Alcohols, esters or hydrocarbons are suitable solvents. The reaction may also be performed by transferring hydrogenation using cyclohexene and palladium. Most preferred reaction reagents may be palladium on charcoal, heptane, and hydrogen.

A representative preferred reaction is illustrated in the schematic below:

The second primary hydroxyl group is then replaced with a terminal leaving group, forming an ester precursor. The conversion of the alcohol to a halide may be accomplished by using acid halides and a base. Suitable acid halides include, but are not limited to, thionyl halides, phosphorus oxychloride, phosphorus trihalides, and oxalyl trihalides. Examples of bases are dimethyl formamide and pyridine. The reaction is performed in hydrocarbon solvents at suitable temperatures ranging from 0° to 70 ° C. Solvents may be selected from among, inter alia, heptane and toluene. The alcohol can be converted to an alkyl or aryl sulfonate leaving group as described above (see page 7 lines 10–25). The resulting alkyl or aryl sulfonate then may be converted to a halide leaving group by reaction with metal halides. Preferred leaving groups include, but are not limited to, halides (resulting in chiral, ester-halide precursor), aryl sulfonates or alkyl sulfonates (most preferably, halide). Representative metal halides include, for example, lithium chloride or bromide or sodium chloride or bromide. Suitable solvents for this transformation may be polar aprotic solvents such as dimethyl sulfoxide and acetone. Preferred reaction temperatures range from 20° to 110° C. A representative of a preferred embodiment of this synthetic step is show below:

1-hydroxy-5-(R)-acetoxyhexane catalytic pyridine
then distill 1-chloro-5-(R)-hydroxyhexane

The terminal leaving group of the ester precursor is replaced with a core moiety substituent (either commercially available or prepared by another synthetic process). Generally, the ester precursor, having a leaving group, and selected nucleophile are reacted in a polar aprotic solvent at a temperature range of +40° to +100° C. Reaction times range from 6 to 24 hours. Representative polar aprotic solvents include, inter alia, dimethyl sulfoxide, acetonitrile, N,N-dimethylformamide. Next, the coupled ester precursor product is quenched with water, followed by extraction into an organic solvent. The organic phase is washed with a salt solution. The ester precursor is isolated by removal of the solvent via distillation. Suitable extraction solvents are esters, including ethyl acetate, propyl acetate, isopropyl acetate, butyl acetate and isobutyl acetate. Although other reagents are within the scope of the invention, preferred reagents include, for example, dimethyl sulfoxide (polar aprotic solvent), 1-chloro-5-(R)-acetoxyhexane (ester precusor), sodium theobromine (nucloephile) and isobutyl acetate (extraction solvent).

Via this process, the ester-protected chiral precursor can be coupled to a hetero atom in a heterocyclic moiety. One example, as shown schematically, couples the ester-protected chiral precursor to the N1 position of theobromine to form a chiral ester of a secondary alcohol with a 3,7-dimethylxanthine moiety.

A schematic representation of this preferred synthesis is shown below.

"theobromine"

+ NaOMe

EtOH

"sodium theobromine"

+ MeOH (R)-5-acetoxy-1-chlorohexane    "sodium theobromine"

DMSO (R)-1-(5-acetoxyhexyl)-3,7-dimethylxanthine

Finally, the ester precursor is reduced to obtain the secondary alcohol product in high yield and purity. The ester precursor is reacted with a mineral acid solution at a temperature ranging from +30° to +100° C. for a period of 0.25 to 6 hours. Examples of mineral acid solutions may be hydrochloric acid in water, methanol or ethanol. Methanol and ethanol are removed by distillation. Water is removed by azeotropic distillation. The intermediate salt is crystallized from a solvent. Representative solvents include, but are not limited to, acetone and methyl ethyl ketone. The salt is neutralized with a base and crystallized from a selected solvent, suitable neutralizing bases being, for example, potassium carbonate, potassium bicarbonate, sodium carbonate, and sodium bicarbonate. Recrystallization solvents include ethyl acetate, propyl acetate, isopropyl acetate, butyl acetate, and isobutyl acetate. Although other reagents are within the scope of the invention, preferred reagents may be methanol/concentrated hydrochloric acid (mineral acid solution), acetone (crystallization solvent), sodium bicarbonate (neutralizing base) and isobutyl acetate (recystallization solvent).

In a preferred embodiment of the inventive process, the chiral secondary alcohol precusor is a protected hydroxyalkyl group 5-(R)-acetoxy-1-chlorohexane ("chloroacetate"), which is subsequently coupled to a 3,7-dimethylxanthinyl moiety at the $N_1$ position to produce a preferred therapeutic agent: 1-(5-(R)-hydroxyhexyl)-3,7-dimethylxanthine. This product is produced with the starting materials ethyl (S)-(–)-lactate to form (R)-(+)-propylene oxide and propargyl alcohol, according to the schematic in FIGS. 1a–1c.

The following examples are illustrative of specific preferred embodiments of the invention; however, these examples are not intended to be construed as limiting the scope of the invention disclosed herein.

EXAMPLE I

This example illustrates the inventive process by showing sucessive process steps in a representative process for preparing a therapeutic chiral secondary alcohol, 1-(5-(R)-hydroxyhexyl)-3,7-dimethylxanthine.

A first reaction step was conducted using the following procedure. A three-necked, 5 L, round bottom flask was fitted with a thermometer, a mechanical stirrer, and a 500 ml addition funnel under argon. Ethyl lactate (472.5 g, 4 mole) and toluene (1.4 L) were added. To the solution was added p-toluenesulfonyl chloride (762.6 g, 4 mole) in portions over 15 minutes with stirring until the solids dissolved. The addition was endothermic (18° C. to 5° C.). After stirring for 45 minutes, the flask was placed in a water bath at 18° C. and triethylamine (610 ml, 4.4 mole) was added dropwise over 2 hours with the reaction temperature kept at or below 30° C. The solution became milky in appearance (triethylamine hydrochloride solid) after half of the triethylamine was added. After stirring 6–8 hours, the reaction slurry was poured into a 1M hydrochloric acid solution (1.75 L) and stirred for 30 minutes. The mixture was separated and the organic phase was washed with saturated aqueous sodium chloride solution (1.75 L). The organic phase was dried over sodium sulfate (5 g). The solvent was evaporated under vacuum to give the tosyl ester (1.1 kg) as a viscous oil. Gas chromatography analysis showed 7% toluene and 0.2% ethyl lactate.

Next, a three-neck, 3 L, round bottom flask, equipped with a mechanical stirrer and addition funnel, was charged with solid sodium borohydride (56.75 g, 1.5 mole), followed by 800 ml dry THF added to the flash, thus forming a slurry. Protocol variation: this reaction step was also run using diisobutylaluminum hydride as the reducing agent in place of sodium borohydride. Ethyl 2-(S)-p-toluenesulfonyloxy propionate (1272 g, 1.0 mole), prepared above, was added slowly. There was a slight temperature rise from room temperature to 40° C. The slurry was cooled to 0° C. and methanol (162 ml, 4 equivalents) was added slowly to keep the reaction mixture from frothing. The reaction mixture was stirred for 2 hours at room temperature after completion of the methanol addition. Upon solidification of the slurry, stirring was stopped.

The reaction was quenched upon slow addition of 10% aqueous HCl (about 30 ml) to pH 4–5. Water (500 ml) was added to dissolve the solids. The saturated aqueous solution was extracted (2×1 L) with ethyl acetate, the organic phases were combined and then dried over sodium sulfate, filtered and the solvents removed under vacuum down (0.1 torr). The yield of crude reaction product (tosyl alcohol) (yield 245 g) was used without further purification.

In a step for preparing a chiral oxirane intermediate, a 250 ml, three-necked, round bottom flask was fitted with a short path condenser connected to a round bottom flask with a dry ice condenser attached. A 50% aqueous potassium hydroxide solution was added and heated to 100° C. with stirring and the crude tosyl alcohol (57.5 g, 0.25 moles) was slowly added. Crude chiral propylene oxide was trapped in the cooled round bottom flask at –70° C. in a dry ice and acetone bath. Once all the tosyl alcohol was added, the pressure was reduced to about 100 mm Hg.

Distillation continued for 30 minutes. The crude chiral propylene oxide was warmed to room temperature and an equal volume of ethylene glycol (20 ml) was added. The ethylene glycol solution was set up with a short path simple distillation apparatus and distilled to give (R)-(+)propylene oxide (7.5 g, yield 52%).

Alternatively, the chiral oxirane may be prepared using an in situ synthetic procedure. Three-necked, 2 L, round bottom flask was fitted with a mechanical stirrer, a dry ice-isopropanol condenser, and a claisen adapter attached to a thermometer, a dropping funnel (250 ml), and an argon inlet. The reaction system was charged with sodium hydride (10.52 g 0.48 mole), DMSO (160 ml) and tetrahydrofuran (40 ml). The flask was cooled to 5° C. (ice bath) and the tosyl alcohol (92 g 0.4 mole) was added (neat) from the dropping funnel with vigorous stirring. The temperature of the flask was maintained between 5°–10° C. during the entire addition (60 minutes). During the addition the reaction mixture turned brown in color. The mixture was stirred for 4 hours at 5°–10° C. until the evolution of hydrogen stopped, indicating that the reaction was complete. To this mixture is added the acetylide anion intermediate.

In preparing the alkynyl intermediate (used as a second reaction product), water (800 ml) was added to sodium hydroxide pellets (800 g) over 20 minutes using a cooling ice bath. The solution was further cooled to 10° C. Hexane (800 ml) and tetrabutylammonium bromide were added followed by propargyl alcohol (237 ml), dropwise over 20 minutes with ice bath cooling. The reaction was allowed to warm to 30° C. during the addition and benzyl chloride (414 ml) was added over 20 minutes, avoiding exothermic conditions. The reaction was warmed to 40° C. for 6 hours at which time gas chromatography analysis indicated all the benzyl chloride had been consumed. After cooling to 25° C., water (800 ml) was added over 10 minutes with ice bath cooling. During this period, the temperature rose to 30° C. The lower, clear aqueous phase was removed and 25% saturated sodium chloride (800 ml) was added to the turbid upper phase. The two phases became clear and the layers were separated. The isolated organic phase was dried with sodium sulphate (20 g) and the hexane evaporated to afford benzyl propargyl ether as an orange oil (515 g, 98.5% pure). The other 1.5% is benzyl ether produced from benzyl alcohol formed in the reaction.

Alternatively, solid potassium hydroxide (12.3 g, 0.22 mole) was stirred with propargyl alcohol (6.0 ml, 0.11 mole) and benzyl chloride (12.8 ml, 0.11 mole) at 60° C. for 16 hours. After cooling to 25° C., hydrochloric acid (80 ml, 3.0M aqueous solution) was added and extracted with hexanes (100 ml, 50 ml). The combined organic extracts were dried over magnesium sulfate and the solvent evaporated. The residue was distilled at 100 torr to afford propargylbenzyl ether as a colorless liquid (bp 140° C., 11.2 g, 71% yield).

In another variation of this process step, p-toluenesulfonic acid monohydrate (0.35 g, 0.002 mole) was added with stirring to ethyl vinyl ether (403 ml, 4.2 mole), which had been cooled to 0° C. Propargyl alcohol (233 ml, 4.0 mole) was added dropwise with cooling over 80 minutes while maintaining the temperature between 12° and 15° C. The reaction was stirred for 10 minutes, following the end of addition, and triethylamine (0.5 ml, 0.003 mole) was added. The crude product (89% pure by GC-MS) was stable as prepared.

Subsequently, preparation of a reactive acetylide anion salt was conducted by the following synthesis. To a three-necked, round bottom flask, fitted with a mechanical stirrer, a thermometer, a dropping funnel, and an argon inlet, was added a solution of benzyl popargyl ether (58.4 g, 0.4 mole) in tetrahydrofuran (140 ml). The flask was cooled to 5° C. (ice bath) and n-butyl lithium (160 ml, 2.5M solution in hexane, 0.4 mole) was added (exothermic reaction and butane gas evolved) at a rate of 0.6 ml per minute for the first 80 ml addition, followed by 1 ml per minute from a syringe (50 ml) using a syringe pump over a period of 3.5 hours. The temperature of the reaction was maintained at 5°–10° C. during the addition using an ice bath. During the addition the color of the reaction turned from light yellow to orange in color. After the addition the reaction mixture was stirred for 60 minutes at 5°–10° C. The acetylide anion thus prepared was then cannulated into a dropping funnel and added to the reaction mixture containing the chiral propylene oxide, prepared above, slowly so as to keep the temperature of the reaction between 5°–10° C. (60 minutes). During the addition, sodium tosylate, previously soluble in DMSO, precipitated out of the solution due to its insolubility in the DMSO-THF-hexane solvent system. After the addition, the reaction mixture was stirred at 5°–10° C. for 4 hours, then warmed to room temperature and stirred overnight (14 hours). The reaction was then cooled to 10° C. and quenched by the slow addition (exothermic reaction) of cold water (600 ml). The organic layer was separated and the aqueous layer was extracted with ethyl acetate (3×150 ml). The combined organic layers were washed with water (200 ml), saturated aqueous sodium chloride solution (200 ml), dried over anhydrous magnesium sulfate (20 g) and concentrated under reduced pressure. Yield was 88 g. Gas chromotagraphy analysis showed the presence of 78% 5-(R)-hydroxy-1-benzyloxy-2-hexyne and 13% of benzylpropargyl ether. The crude product was used without purification.

Next, acetic anhydride (23.6 ml, 0.25 mole) and sulfuric acid (0.13 ml) were added to stirred 5-(R)-hydroxy-1-benzyloxy-2-hexyne (34 g, 0.17 mole), prepared above, at 25° C., and the reaction was heated to 60° C. for 20 hours. Water (100 ml) was added, followed by solid sodium bicarbonate (33 g, 0.40 mole) in portions. The reaction mixture was extracted with ethyl acetate (80 ml), the solvent dried (magnesium sulfate) and evaporated to afford 5-(R)-acetoxy-1-benzyloxy-2-hexyne (41.1 g, 99% yield) as a brown oil.

Two variations on the immediately preceding procedure for preparing a second intermediate alcohol. The second variation also provides an intermediate ester. The procedure was conducted by adding DMSO (100 ml) to 95% lithium amide (4.68 g, 0.19 mole) at 20° C., heating to 60° C. over 30 minutes and maintaining 60° C. for 30 minutes when ammonia evolution ceased. The mixture was cooled to 10° C. over 20 minutes and benzyl propargyl ether (26.3 g, 0.18 mole) was added over 25 minutes with the temperature being increased to 15° C. The reaction was stirred for 20 minutes while cooling to 2° C. (R)-propylene oxide (11.6 ml, 0.20 mole) was added over 20 minutes and the reaction mixture was warmed to 20° C. over 20 minutes. The reaction was stirred for 8 hours at 20° C. Hydrochloric acid (1M aqueous solution, 200 ml) and ethyl acetate (200 ml) were added to stop the reaction and the temperature was increased to 40° C. After cooling to 20° C., the phases were separated (lower phase orange syrup, upper phase brown liquid, defined interphase) and ethyl acetate was washed with a 25% saturated sodium chloride solution (2×100 ml), dried (magnesium sulfate, 5.0 g) and the solvent evaporated at 60° C. (100 torr) to afford 5-(R)-hydroxy-1-benxyloxy-2-hexyne as a brown oil (36 g, 97% yield, 95% pure by gas chromatography).

A second variation was initiated by adding DMSO (1000 ml) to 95% lithium amide (87.1 g, 3.60 mole) at 20° C. over 10 minutes without an exothermic reaction, heated to 60° C. over 30 minutes and maintained at that temperature for 30 minutes when ammonia evolution had ceased. The mixture was cooled to 15° C. over 20 minutes and acetaldehyde ethyl propargyl acetal (580 ml, 3.50 mole) was added to the resulting slurry over 40 minutes with cooling in an ice bath and maintaining the temperature at 15° C. The reaction mixture was stirred for 20 minutes while cooling to 2° C., and chiral R-(+)-propylene oxide (252 ml, 3.60 mole) was added over 120 minutes with ice bath cooling. The temperature was increased to 20° C. The reaction was maintained at 20° C. for 120 minutes and an aliquot removed was shown to be 94.6% 5-(R)-hydroxy-1-ethoxyethoxy-2-hexyne by GC-MS. Acetic anhydride (570 ml, 6.0 mole) was added over 45 minutes with ice bath cooling and the temperature increased to 30° C. The reaction was stirred at 60° C. for 16 hours. Saturated sodium bicarbonate (500 ml) was added, followed by solid sodium bicarbonate (700 g, 8.3 mole) in 50 g portions. Water (1000 ml) and ethyl acetate (1000 ml) were added, the phases separated and the ethyl acetate phase was washed with 25% saturated sodium chloride solution (2×800 ml). The solvent was removed to afford a residue of crude 5-(R)-acetoxy-1-ethoxyethoxy-2-hexyne (680 g, 85% yield).

Alternatively, to a 300 ml round bottomed flask fitted with a magnetic stirbar, a dropping funnel and an argon inlet were placed the 5-(R)-hydroxy-1-benzyloxy-2-hexyne (88 g, 0.43 mole), triethylamine (91 ml, 0.64 mole), and dimethylaminopyridine (2 g; 0.016 mole) and then the flask was cooled to 10° C. using an ice bath. Acetic anhydride (49 ml, 0.52 mole) was added dropwise (exothermic reaction) maintaining the temperature of the reaction at 10° C. by external cooling using an ice-water bath. After the addition, the cooling bath was removed and the reaction mixture was warmed to room temperature and stirred overnight (12 hours). The reaction was cooled to 10° C. and methanol (30 ml) was added (exothermic reaction) to decompose excess acetic anhydride. The mixture was stirred for 60 minutes, water (200 ml) was added, and then the mixture was extracted with ethyl acetate (3×75 ml). The combined organic layers were washed with saturated sodium bicarbonate solution (50 ml), water (50 ml), saturated aqueous sodium chloride solution (50 ml), dried over anhydrous $MgSO_4$ (10 g), and then concentrated under reduced pressure (yield=90 g, gas chromatography analysis showed a presence 80% 5-(R)-acetoxy-1-benzyloxy-2-hexyne and 13% of benzylpropargyl ether). The crude product was used without further purification.

Hydrogenation of the alkynyl, unsaturated bond was accomplished by one of the two representative methods. Raney nickel (17.6 g of slurry, 10% by weight to the substrate) was added under argon to a Pyrex® hydrogenation vessel and then a solution of 5-(R)-acetoxy-1-benzyloxy-2-hexyne (88.7 g, 0.36 mole) in ethanol (90 ml) was added. The reaction vessel was attached to a Parr® shaker and filled with hydrogen (75 psi), shaken for five minutes and evacuated and this process was repeated again and finally the reaction vessel was brought to 75 psi with hydrogen and shaken for 12 hours. An exothermic reaction and rapid absorption of hydrogen was observed during the first 2–3 hours. As hydrogen was consumed and the pressure in the vessel was returned to 75 psi. After 12 hours the reaction mixture was filtered. Raney nickel was always kept under a layer of solvent (pyrophoric when it is dry). The residue was rinsed with ethyl acetate (3×75 mi). The combined filtrates were concentrated under reduced pressure to give 80 g of the crude product which was further purified by fractional distillation. Initial fraction (10.3 g, 90°–120° C./2.5 mm pressure) contained 70% propylbenzyl ether and 12% 5-(R)-acetoxy-1-benzyloxyhexane and the second fraction (65.5 g, 134° C./2.5 mm pressure) contained 96% pure (by gas chromotagraphy) 5-(R)-acetoxy-1-benzyloxyhexane.

Alternatively, hydrogenation was run using a mixture of Raney nickel (10 g of slurry) and 5-(R)-acetoxy-1-ethoxyethoxy-2-hexyne (40 g, 0.17 mole) in ethanol (100 ml). The mixture was shaken with hydrogen gas (60 psi) on a Parr shaker for 5 hours. After filtration of the catalyst, the filtrate was evaporated under vacuum. Residual oil was dissolved in hexanes (100 ml) and the mixture was filtered to remove suspended particles. Evaporation of the solvent under reduced pressure provided 5-(R)-acetoxy-1-ethoxyethoxyhexane (40 g).

Next, the alkali-stable group was converted to a primary hydroxyl group in one of two representative alternative processes. Palladium (10%) on carbon (3.2 g) was added to a Pyrex® hydrogenation vessel and a solution of 5-(R)-acetoxy-1-benzyloxyhexane (65.5 g, 0.26 mole) in acetic acid (65 ml) was added under an argon atmosphere. The reaction vessel was filled with hydrogen gas (75 psi), shaken for five minutes, evacuated, and this process was repeated again and finally the reaction vessel was brought to 75 psi with hydrogen and hydrogenated for 12 hours. Exothermic reaction and rapid absorption of hydrogen was observed during first 2–3 hours. The vessel was replenished with hydrogen whenever the hydrogen was consumed. After 12 hours the reaction mixture was filtered, and the solids were washed with ethyl acetate (75 ml). The combined filtrates were concentrated under reduced pressure and then the residue was dissolved in ethyl acetate (200 ml). The solution was washed with saturated aqueous sodium bicarbonate solution (2×100 ml) and saturated aqueous sodium chloride solution (100 ml) and then dried over magnesium sulfate (10 g). Evaporation of the solvent under reduced pressure gave 39.84 g of 5-(R)-acetoxy-1-hydroxyhexane (yield=95%, 91% pure by gas chromotagraphy).

Alternatively, a solution of 5-(R)-acetoxy-1-ethoxyethoxyhexane (80 g, 0.34 mole) in ethyl lactate (150 ml) was stirred with 1M of aqueous hydrochloric acid solution (100 ml). After 4 hours, the layers were separated and the aqueous layer was saturated with sodium chloride and then extracted with ethyl lactate (4×75 ml). The combined organic layers were washed with saturated aqueous sodium bicarbonate solution (2×100 ml), dried over magnesium sulfate and the solvent evaporated under vacuum to give 5-(R)-acetoxy-1-hydroxyhexane (46 g, 83% yield).

In further synthetic protocol variation, the above steps were completed as a single step, provided that hydrogen and palladium on carbon is used to reduce 5-(R)-acetoxy-1-benzyloxy-2-hexyne to 5-(R)-acetoxy-1-hydroxyhexane.

Next, a second primary hydroxyl group (the 1 hydroxyl moiety of 5-(R)-acetoxy-1-hydroxyhexane) is replaced with a terminal leaving group. Procedurally 5-(R)-acetoxy-1-hydroxyhexane (39.84 g, 0.249 mole) was added to a 300 ml round bottomed flask fitted with a magnetic stirbar, a dropping funnel, and an outlet connected to a bubbler. Thionyl chloride (20 ml, 0.27 mole) was added dropwise (exothermic reaction) from the dropping funnel. The temperature of the reaction was maintained at 20°–23° C. by external cooling using ice-water bath. During the addition the reaction turned light brown in color and hydrogen chloride gas was evolved. After the addition, pyridine (2.5 ml, 0.03 mole) was added very slowly (exothermic reaction), the cooling bath was removed and the reaction mixture was warmed to 60°–70° C. for 3 hours. Sulfur dioxide was evolved and completion of the reaction was indicated by the cessation of gas evolution. The reaction was cooled to room temperature and pyridine hydrochloride, formed during the reaction, crystallized out of the reaction. Hexane (100 ml) was added and the reaction mixture was washed with water (2×50 ml), saturated aqueous sodium bicarbonate solution (2×50 ml), water (50 ml), saturated aqueous sodium chloride solution (50 ml); dried over anhydrous $MgSO_4$ (10 g); and then concentrated under reduced pressure. Further purification was done by fractional distillation (bp 75° C. at 2.5 mm pressure, yield=32.71 g (67%), chemical purity 95% by gas chromotagraphy, enantiomeric excess 93%).

In an alternative procedure, methanesulfonyl chloride (24.3 ml, 0.31 mole) was added dropwise to a mixture of 1-hydroxy-5-(R)-acetoxyhexane (45.7 g, 0.28 mole) and triethylamine (60 ml, 0.43 mole) in ethyl acetate (300 ml), which had been cooled to 5°–10° C., and the resulting mixture stirred at 10° C. for 1 hour. Saturated aqueous sodium chloride solution (100 ml) and water (100 ml) were added and the organic layer was separated. The aqueous layer was extracted with ethyl acetate (3×100 ml). The combined organic layers were washed with saturated aqueous sodium chloride solution, dried over magnesium sulfate, and then the solvent was evaporated under vacuum to give an oil (63 g). To a solution of oil in DMSO (300 ml) was added sodium chloride (84 g, 1.4 mole). The reaction mixture was heated at 60° C. for 8 hours. After cooling to ambient temperature, cold water (500 ml) and ethyl acetate (500 ml) were added and the mixture was stirred for 10 minutes. The organic layer was separated and the aqueous-DMSO layer was extracted with ethyl acetate (3×100 ml). The combined organic layers were washed with water (2×100 ml), washed with saturated aqueous sodium chloride solution (100 ml), and then dried over magnesium sulfate. After evaporation of the solvent under vacuum, the oil was fractionally distilled (74°–78° C., 3 minutes) to give 1-chloro-5-(R)-acetoxy (25 g, 66% yield) as a clear oil.

Figure 1A:
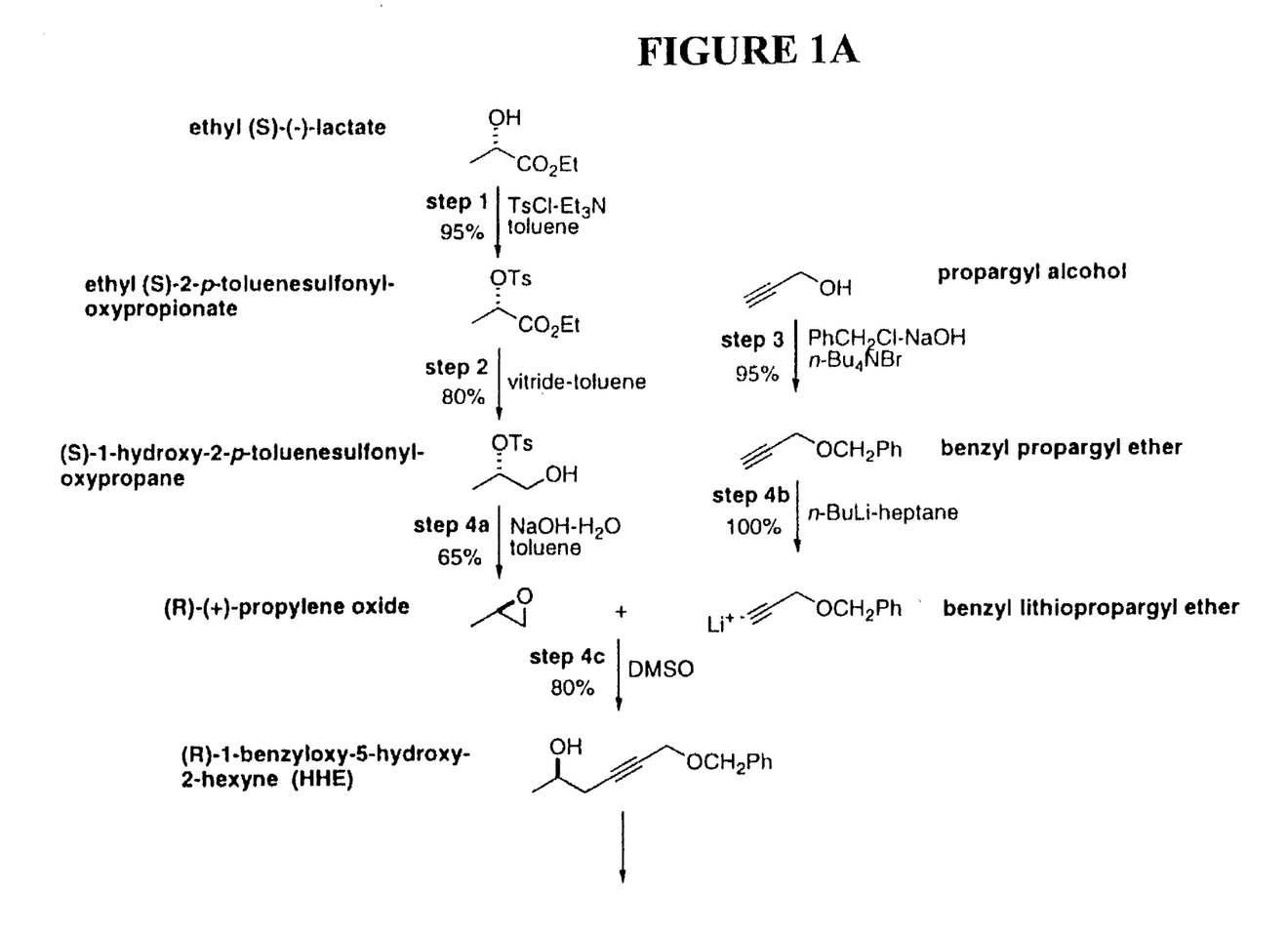
Figure 1B:
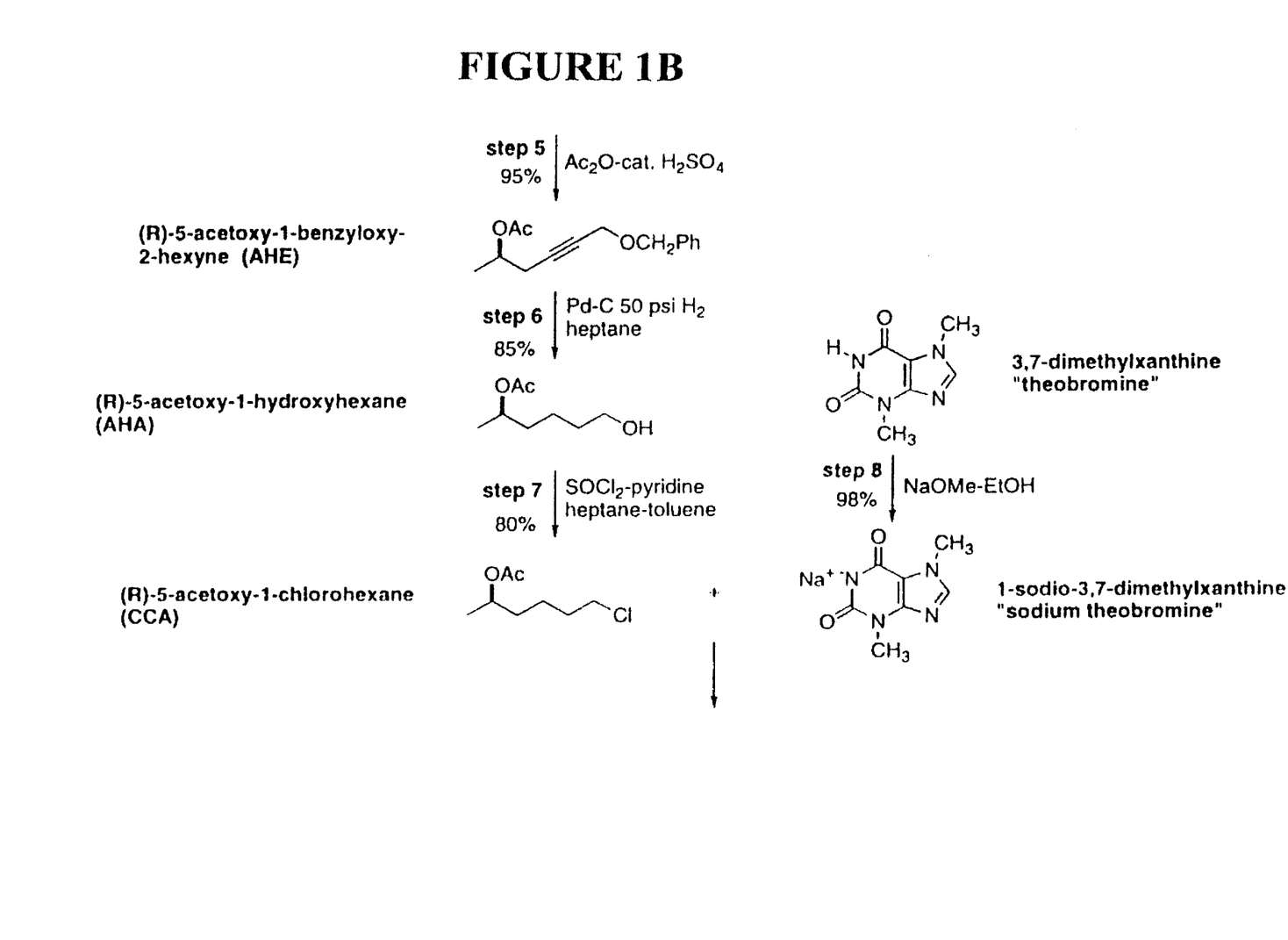

The 1-chloro-5-(R)-acetoxyhexane was then coupled to a theobromine nucleophile by reacting with sodium theobromine. The resulting acetoxydimethylxanthine was then hydrolyzed to obtain the desired secondary alcohol (as illustrated in FIGS. 1a–1c).

COMPARATIVE EXAMPLE

This example illustrates a comparative synthesis of a conventional process (representing a process as disclosed in Johnston, et al., supra) for preparing a chiral oxirane intermediate product, (R)-(+)-methyloxirane. As shown in the comparative results of this synthetic protocol, this comparative process is not suitable for larger-scale production processes and results in lower yield and product impurities, when compared with inventive process.

Procedurally, at 0° C. with mechanical stirring, ethyl S-(−)-lactate (303 g, 2.56 mol) was dissolved in pyridine (3 L). p-Toluenesulfonyl chloride (595 g, 3.12 mol) was added in 100 g portions over 20 minutes. The red solution was stirred for 1 hour at 0° C., and then allowed to stand at a temperature ranging from 4° to 7° C. for 24 hours. The resulting reaction mixture was poured into ice water (3.5 L water and 500 g ice). Water (0.5 L) was added and the mixture was warmed to room temperature and then extracted with diethyl ether (6 L). The phases were separated and the organic phase was washed with 1N aqueous hydrochloric acid (4 L), saturated aqueous copper(II) sulfate solution (4 L), water (4 L), and saturated aqueous sodium chloride solution (4 L). The solution was dried over anhydrous sodium sulfate (100 g), filtered, and the solvents were removed under vacuum to give ethyl 2-O-p-toluenesulfonyl-S-(−)-lactate (634.63 g, 91% yield) as a red oil.

Next, ethyl 2-O-p-toluenesulfonyl-S-(−)-lactate (557.44 g, 2.05 mol), prepared above, was dissolved in anhydrous tetrahydrofuran (200 mL) with mechanical stirring, under an argon atmosphere. To the tetrahydrofuran solution, a 1M solution of borane in tetrahydrofuran (4.1 L, 4.1 mol) was added dropwise. The solution was stirred for 5 days at room temperature and then heated to 60° C. for 24 hours, resulting in evolution of hydrogen gas. After cooling to room temperature, the solution was carefully poured into water (4

L). Sodium carbonate (40 g, 0.38 mmol) was added to the aqueous tetrahydrofuran solution to break the emulsion. The solution was extracted with diethyl ether (2×3 L) and the combined organic phases were washed with saturated aqueous sodium chloride solution (3 L). After drying over magnesium sulfate (100 g) and filtering, the solvents were removed under reduced pressure to give (S)-1-hydroxy-2-p-toluenesulfonyloxypropane (400 g, 100% yield).

This process step was a lengthy process, requiring a total of six days to complete, compared to one day, as required in a corresponding process step in the inventive synthetic protocol. In addition, this conventional process required a 4 L reaction volume of borane, nearly 20 times the reaction volume of starting material (200 mL)! In this conventional process step, hydrogen gas evolution also presented a problem, suggesting difficulting in scaling-up the comparative process for commercial applications.

Subsequently, the crude (S)-1-hydroxy-2-p-toluenesulfonyloxypropane (400 g, 2.05 mol), prepared above was added dropwise to a 50% aqueous potassium hydoxide solution (80 g in 160 mL water) at 70° C. The (R)-(+)-methyloxirane distilling from the reaction flask was collected in a flask cooled in a dry ice-acetone bath and fitted with a dry ice condenser. The crude (R)-(+)-methyloxirane was further purified by distillation from potassium hydroxide (50 g) to give (R)(+)-methyloxirane (97.64 g, 82% yield) as a clear liquid.

Generally, several issues resulted from Johnston et al.'s disclosed preparations. An initial preparation only provided ~10% yield, which may have resulted from the substantial solvent volume required to induce crystallization. In addition, on a laboratory scale, inducing crystallization spanned 2 days, and when scaled up, took 9 days! Three sequential crystallizations of mother liquor were required to obtain a 91% yield.

In preparing tosyl alcohol from the lactate intermediate, if the reaction mixture in Johnston et al. was not heated, the reaction time spanned 8 days, 5 days at room temperature and 3 days at 40° C. Of most difficulty was the exothermic conditions resulting from addition of borane-THF. The reaction mixture was not contained in the round bottom in which it was prepared. In addition, upon subsequent heating, a large volume of gas was generated. Finally, large volumes of hydrogen gas evolved during the reaction when quenched with water.

In preparing the disclosed methyloxirane in the above process from the tosyl alcohol, average yields ranged from 40–50% and purification and quantification are difficult because of physical limitations of distillation apparatus and multiple, sequential distillations.

As discussed in detail, this comparative method step requires procedures that are not readily adaptable for scaled-up commercial applications, primarily distillation of large volumes of product. Instead, the inventive process for preparing chiral epoxide products preferably utilizes more commercially-viable purification and isolation techniques.

Other comparative processes, although not exemplified in a Comparative Example, are discussed in detail above and differ from the inventive process as shown in the following paragraphs.

Mori et al.'s specific preparation of tosyl ethyl lactate (discussed above) uses an excess of tosyl chloride (1.2 equivalents), which is not required by the inventive process. In contrast, the inventive process utilizes an excess of α-hydroxy ester. Furthermore, the Mori et al. process specifically utilitizes cold temperatures ranging from −5° to −10° C. and 7° C. overnight. In a preferred process of the invention, the reaction is cooled only to 20° C. and the temperature subsequently maintained at 28°–30° C. The inventive process permits significantly shorter reaction times, in comparison to the process disclosed in Mori et al. (e.g., 25 hours vs. 3–4 hours after addition of triethylamine).

In Mori et al., 5 sequential washes are used in comparison to two simple brine washes and use of diethyl ether as an isolation solvent is not practical industrially. Whereas in a preferred inventive process a tosyl ethyl lactate is isolated in toluene, Mori et al. crystallizes the intermediate product.

In reducing the disclosed tosyl ethyl lactate, Mori et al. require a 5-day reaction time, versus as little as a 2-hour reaction time (after addition of reducing agent) in the inventive process! Mori et al. specifically discloses addition of tosyl alcohol to aqueous potassium hydroxide (50%), which requires two, serial distillations. In a preferred inventive process, the intermediate primary alcohol is reacted in an organic solvent with an aqueous base solution and the resulting intermediate chiral epoxide product is extracted into an organic solvent and fractionally distilled. Moreover, Mori et al. discloses much higher reaction temperatures (70° vs. 20° C.). Mori et al. discloses a limited yield of 65% and an ee of 97% (determined by optical rotation). In contrast, a preferred inventive process permits yields as high as 80% and ee of greater than 98% (determined by GC).

Similar to Mori et al.'s specific preparation of tosyl ethyl lactate, Hillis et al (discussed above) discloses use of a large excess of solvent, in proportion to α-hydroxy ester (1 liter of toluene to 0.7 moles tosyl ethyl lactate), whereas the inventive process does not require this substantial solvent excess. Again, Hillis et al. reaction temperatures are significantly colder than provided for in preferred processes of the invention (−15° C. vs. 28°–30° C.).

In reducing the mesyl ethyl lactate, Hillis et al. filters aluminum salts formed in the reaction. In a preferred inventive process, contaminating aluminum salts are dissolved with acid, the resulting intermediate primary alcohol isolated from an organic solvent. Furthermore, Hillis et al. do not isolate the mesyl chloride product. These disclosed process steps provide a yield of 72% as compared with a yield of the inventive process as high as 80%.

As discussed above, Ellis, et al. discloses the preparation of an (S)-(−)-propylene oxide by generating a diol from ethyl lactate and converting the diol to a bromoacetate intermediate, which is subsequently reacted to obtain the disclosed propylene oxide. In contrast to this specific disclosed reaction, the inventive process instead prepares a chiral epoxide intermediate product through an intermediate primary alcohol.

We claim:

1. A process for asymmetric synthesis of chiral secondary alcohol products, comprising the steps of:

(1) providing a chiral α-hydroxy ester starting material of variable chain length, wherein a starting material stereochemistry is opposite a secondary alcohol product stereochemistry;

(2) activating the starting material hydroxyl group with a leaving group;

(3) converting the starting material ester group to a first intermediate alcohol, (4) reducing the first intermediate alcohol with a base in an intermolecular reaction between the first intermediate alcohol and the leaving group, forming a chiral oxirane and inverting the starting material stereochemistry, (5) providing a terminal, $C_{3-10}$ alkynyl primary alcohol, having a first primary hydroxyl group;

(6) converting the first primary hydroxyl group to an alkali-stable group to form an alkynyl intermediate, (7) treating the alkynyl intermediate with a strong base and forming an acetylide anion salt having a mono- or di-valent cation, (8) coupling the acetylide anion salt and chiral oxirane from step (4), forming a second intermediate alcohol, having alkynyl and alkali-stable groups, (9) converting the hydroxyl group of the second intermediate alcohol to an intermediate ester, having the alkynyl and alkali-stable groups, (10) hydrogenating the unsaturated alkynyl bond to a saturated bond, (11) converting the alkali-stable group to a second primary hydroxyl group, (12) replacing the second primary hydroxyl group with a terminal leaving group to form an ester presursor, (13) replacing the terminal leaving group of the ester precursor with a nucleophilic moiety that displaces the terminal leaving group in a substitution reaction, and (14) reducing the ester precursor to obtain the secondary alcohol product.

2. The process of claim 1, wherein the $C_{3-10}$ alkynyl primary alcohol is reacted with an electrophile to form the alkynyl intermediate.

3. The process of claim 1, wherein the acetylide anion is coupled to the chiral oxirane in a suitable solvent at temperatures ranging from –20° to 65° C.

4. The process of claim 3, wherein the reagents are dimethylsulfoxide, N-methylpyrrolidinone and lithium perchlorate in tetrahydrofuran/hexane.

5. The process of claim 3, wherein the temperature selected results in a regioselectivity ranging from 99.65 to 99.85%.

6. The process of claim 1, wherein the second intermediate alcohol is reacted with an acid anhydride or acid halide in the presence of acids or bases to obtain the intermediate ester.

7. The process of claim 1, wherein hydrogenating the unsaturated alkynyl bond comprises:

a) treating the intermediate ester to remove impurities; and b) reducing the unsaturated bond using a transition metal catalyst and hydrogen at elevated pressures.

8. The process of claim 1, wherein converting the alkali-stable group to a primary hydroxyl group is accomplished by hydrogenolysis or mild acid hydrolysis of the alkali-stable group, protecting the primary hydroxyl group.

9. The process of claim 1, wherein the second primary hydroxyl group is replaced with a terminal leaving group using an acid halide and a suitable base.

10. The process of claim 1, wherein the chain length of the chiral α-hydroxy ester is from about 3 to about 10 carbon atoms long.

11. The process of claim 1, wherein the leaving group is a tosylate or a mesylate.

12. The process of claim 1, wherein the alkali-stable group is an acetal or a substituted or unsubstituted benzyl group.

13. The process of claim 1, wherein the mono- or di-valent cation is a lithium, sodium, potassium or magnesium ion.

14. A process for preparing a chiral epoxide comprising the steps of:

a) converting an α-hydroxy ester starting material to an intermediate activated ester by esterification, using an excess of the α-hydroxy ester, thereby activating the α-hydroxy ester moiety with a preselected leaving group, while maintaining the original stereochemistry of the ester starting material;

b) reducing a terminal ester moiety of the intermediate activated ester to a corresponding intermediate primary alcohol; and c) allowing the intermediate primary alcohol to react with a base to form a corresponding alkoxide anion, thereby permitting the corresponding alkoxide anion to displace the preselected leaving group, invert the original stereochemistry and form the chiral epoxide having a final stereochemistry opposite the original stereochemistry of the α-hydroxy starting material.

15. The process of claim 14, wherein the converting step a) comprises: combining starting material with a sulfonyl acid chloride in the presence of a base at a reaction temperature ranging from 20°–50° C. for a period ranging from four to eight hours;

adding a mineral acid to remove any excess base;

washing an organic phase with a salt solution; and eliminating the solvent to isolate the intermediate activated ester.

16. The process of claim 15, wherein a solvent is used in the combining step.

17. The process of claim 16, wherein the solvent is an ester, ether or hydrocarbon solvent.

18. The process of claim 15, wherein the sulphonyl acid chloride is p-toluenesulfonyl chloride or methanesulfonyl chloride.

19. The process of claim 15, wherein the base is a pyridine or trialkylamine, the mineral acid is hydrochloric acid and the salt solution is sodium chloride or calcium chloride.

20. The process of claim 15, wherein the reaction temperature ranges from 25° C. to 30° C.

21. The process of claim 15, wherein the solvent is eliminated by evaporation.

22. The process of claim 14, wherein the reducing step b) comprises:

mixing the intermediate activated ester with a solvent to form a reaction mixture adding a reducing agent to the reactionmisture at an addition temperature ranging from –40° C. to +80° C.;

stirring for a period ranging from one hour to five days;

adding a ketone to remove any excess reducing agent;

adding a predetermined amount of a solubilizing agent to hydrolize any reducing agent residue at a hydrolyzing temperature ranging from 0° to 40° C.;

filtering the reaction mixture to remove any solids precipitated;

washing the reaction mixture with an aqueous solution; and removing the solvent to isolate the intermediate primary alcohol.

23. The process of claim 22, wherein the solubilizing agent is selected from the group consisting of sodium carbonate, sodium hydroxide, hydrochloric acid, sulfuric acid and potassium sodium tartrate.

24. The process of claim 22, wherein the solvent is an ether or hydrocarbon solvent, and the reducing agent is selected from the group consisting of sodium borohydride activated with methanol or acetic acid, borane-tetrahydrofuran, borne-methyl sulfide, diisobutylaluminum hydride and sodium bis(2-methoxyethoxy)aluminum hydride.

25. The process of claim 14, wherein step c) comprises:

mixing the intermediate primary alcohol with a quantity of solvent to form a reaction solution;

adding the base to the reaction solution, while maintaining a solution temperature of between 0° C. and 90° C.; and isolating the chiral epoxide.

26. The process of claim 25, wherein the solvent is a polar aprotic solvent, water, ether or an alcohol.

27. The process of claim 25, wherein the base is selected from the group consisting of sodium hydroxide, potassium hydroxide, calcium hydroxide, sodium hydride, sodium carbonate, potassium carbonate and an alkoxide base.

28. The process of claim 25, wherein isolating the chiral epoxide comprises:

distilling the chiral epoxide from the reaction solution; or extracting the chiral epoxide into an organic extraction solvent and subsequently distilling the chiral epoxide from the extraction solvent, wherein either distillation step occurs at a distillation temperature ranging from 25° C. to 100° C.

29. The process of claim 1, wherein steps (8) and (9) include: i) coupling the acetylide anion salt to the chiral oxirane; and 2) subsequently converting the hydroxyl group of the second intermediate alcohol to an intermediate ester in situ.

30. The process of claim 29, wherein a solvent in steps (8) and (9) is N-methyl pyrrolidinone.

* * * * *